US012722006B2

(12) United States Patent
Gutierrez et al.

(10) Patent No.: US 12,722,006 B2
(45) Date of Patent: Sep. 1, 2026

(54) MULTIDIRECTIONAL PERIOCULAR NERVE STIMULATION AND ASSOCIATED SYSTEMS, DEVICES, AND METHODS

(71) Applicant: Verily Life Sciences LLC, Dallas, TX (US)

(72) Inventors: Christian Gutierrez, South San Francisco, CA (US); Bo Lu, South San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 671 days.

(21) Appl. No.: 17/707,606

(22) Filed: Mar. 29, 2022

(65) Prior Publication Data

US 2022/0313999 A1 Oct. 6, 2022

Related U.S. Application Data

(60) Provisional application No. 63/168,979, filed on Mar. 31, 2021.

(51) Int. Cl.
*A61N 1/36* (2006.01)
*A61N 1/05* (2006.01)

(52) U.S. Cl.
CPC ....... *A61N 1/36046* (2013.01); *A61N 1/0526* (2013.01); *A61N 1/0551* (2013.01)

(58) Field of Classification Search
CPC . A61N 1/36046; A61N 1/0526; A61N 1/0551
See application file for complete search history.

(56) References Cited

U.S. PATENT DOCUMENTS

2008/0288037 A1* 11/2008 Neysmith .............. H05K 1/115 607/116
2012/0130398 A1* 5/2012 Ackermann ......... A61N 1/3787 606/129
2014/0371565 A1* 12/2014 Glasser ................ A61B 5/6821 600/383
2016/0158562 A1 6/2016 Bornzin et al.
(Continued)

OTHER PUBLICATIONS

International Searching Authority/US, International Search Report and Written Opinion, PCT Application No. PCT/US22/22478, International Search Report Mail Date Sep. 14, 2022, 11 pages.

*Primary Examiner* — Lynsey C Eiseman
*Assistant Examiner* — Skylar Lindsey Christianson
(74) *Attorney, Agent, or Firm* — Christensen O'Connor Johnson Kindness PLLC

(57) ABSTRACT

A device may be configured to be located underneath an eyelid for treating ophthalmic conditions. The device may include an annular body and a flex circuit mounted on and conforming to at least a portion of an outer surface of the annular body. The flex circuit may include a substrate comprising an electronic circuitry portion and one or more electrode portions, and electronic circuitry attached to the electronic circuitry portion of the substrate. The flex circuit may further include one or more electrodes bonded to the substrate at the one or more electrode portions and electrically coupled to the electronic circuitry. An orientation around the annular body of each of the one or more electrodes may be based on a position on the substrate of a respective electrode portion of the one or more electrode portions.

19 Claims, 11 Drawing Sheets

(56) References Cited

U.S. PATENT DOCUMENTS

| | | | | |
|---|---|---|---|---|
| 2017/0031159 | A1* | 2/2017 | Pugh | G02B 27/0093 |
| 2018/0116872 | A1 | 5/2018 | Kahook | |
| 2019/0143116 | A1* | 5/2019 | Mowery | A61N 1/0476<br>607/53 |
| 2020/0306538 | A1 | 10/2020 | Gutierrez | |
| 2020/0391029 | A1* | 12/2020 | Mullins | A61N 1/36014 |

* cited by examiner

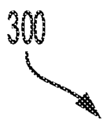

| | |
|---|---|
| Form planar flex circuit into curved shape | 305 |
| Mount formed flex circuit on close up to polymer filament | 310 |
| Insert mounted flex circuit and polymer filament subassembly into polymer sheath | 315 |
| Position heat shrink tube around sheathed subassembly | 320 |
| Apply heat to heat shrink tube and bond polymer sheath to flex circuit and polymer filament | 325 |
| Remove heat shrink tubing | 330 |
| Ablate polymer sheath to expose portions of electrode surfaces of on the flex circuit | 335 |
| Mold assembly into annular shape | 340 |

MULTIDIRECTIONAL PERIOCULAR NERVE STIMULATION AND ASSOCIATED SYSTEMS, DEVICES, AND METHODS

CROSS-REFERENCE TO RELATED APPLICATIONS

The present disclosure claims priority to and the benefit of U.S. Provisional Patent Application No. 63/168,979, filed Mar. 31, 2022, the entirety of which is incorporated by reference herein.

TECHNICAL FIELD

The present disclosure relates generally to ophthalmic systems and devices and associated methods for stimulating nerves in and/or around the eye, and, in particular but not exclusively, relates to systems and devices and associated methods for placement in a periocular space, and out of the field of vision, for stimulating ocular or periocular tissues to treat ophthalmic conditions.

BACKGROUND

A large number of people have Dry Eye Disease ("DED"), which includes symptoms of intense pain, stinging eyes, foreign body sensation, light sensitivity, blurriness, increased risk of infection, and possible vision loss.

DED is characterized by insufficient tear volume on the ocular surface of a patient, which is generally caused by insufficient tear production or excessive tear evaporation. Insufficient tear volume results in tear hyperosmolarity, which causes inflammation and nerve damage and can lead to progressive loss of tear production and quality.

Dry-eye symptoms vary based on a variety of factors. For example, dry-eye symptoms vary throughout a day in response to diurnal physiological variations in tear pH, intraocular pressure, corneal sensitivity, visual sensitivity, and melatonin production. For instance, corneal sensitivity is often significantly greater in the evening than compared to the morning. Longer term variations in dry-eye symptoms can be related to use of systemic medications, chronic disease (e.g., diabetes), hormonal changes, and aging. Changes to a patient's environment also contribute to dry-eye symptom variations. For example, dry-eye symptoms can increase due to low humidity of air-conditioned offices, winter heating, computer use, phone use, allergens, and contact lenses.

Current approaches to treatment of dry-eye symptoms do not or cannot account for the variety of factors that impact the severity and onset of the symptoms, as current treatment for DED is primarily eye-drop based and provides only limited episodic and temporary relief.

SUMMARY

The present disclosure advantageously describes devices, systems, and methods for treating dry eye. According to some aspects, a device is presented that is configured to be located underneath an eyelid and worn by a user for treating dry eye. In some embodiments, the device includes a plurality of stimulation electrodes positioned at various positions around a circumference of the device. The stimulation electrodes may be oriented in different directions relative to a central axis of the device, such as inward toward the central axis, or outward away from the central axis. The positions and orientations of the electrodes may correspond to a nerve, nerve group, or tissue structure (e.g., lacrimal gland) to be treated. The device may further include an antenna configured to receive electromagnetic energy from a wireless remote control device, and electronic circuitry configured to receive electrical power from the antenna and to activate one or more of the electrodes according to one or more operating parameters associated with a treatment regimen.

According to one embodiment of the present disclosure, a device is configured to be worn on an eye of a patient for stimulating nerves in and around the patient's eye, the device including: an annular body comprising a circumference surrounding a central axis of the annular body; a first electrode positioned at a first angular position of the circumference, the first electrode comprising a first exposed electrode surface facing toward the central axis of the annular body; a second electrode positioned at a different second angular position of the circumference, the second electrode comprising a second exposed electrode surface facing away from the central axis of the annular body; and one or more electronic components coupled to the annular body and configured to provide electrical power to the first electrode and the second electrode to stimulate the nerves.

In some embodiments, the annular body comprises a toroidal shape, where the first electrode is positioned on an inward-facing portion of the toroidal shape, and where the second electrode is positioned on an outward-facing portion of the toroidal shape. In some embodiments, the toroidal shape comprises a tubular circumference, where the first exposed electrode surface extends over a first portion of the tubular circumference, and where the second exposed electrode surface extends over a different second portion of the tubular circumference. In some embodiments, the device further includes a counter electrode including a third exposed electrode surface facing away from the central axis of the annular body, where the first electrode, the counter electrode, and the one or more electronic components are configured to provide an electrical circuit extending through the patient's tissue. In some embodiments, the device further includes an antenna extending along the annular body, where the antenna is configured to receive electromagnetic energy and provide an electrical current to the first electrode and the second electrode.

In some embodiments, the device includes: an electrical subassembly including: an elongate flexible substrate; the first electrode mounted at a first location of the elongate flexible substrate, the first location corresponding to the first angular position; the second electrode mounted at a different second location of the elongate flexible substrate, the second location corresponding to the second angular position; and the one or more electronic components mounted at a different third location of the elongate flexible substrate. In some aspects, the annular body comprises a filament comprising an annular shape, and the electrical subassembly is attached to the filament. In some embodiments, the device further includes a tubing positioned over the electrical subassembly and the filament, where the tubing comprises a first opening and a second opening, where the first exposed electrode surface is exposed through the first opening, and where the second exposed electrode surface is exposed through the second opening.

In some embodiments, the electrical subassembly further includes: a first conductive trace disposed in the flexible substrate, the first conductive trace electrically coupling the one or more electronic components to at least one of the first electrode or the second electrode; and an antenna comprising a second conductive trace disposed in the flexible substrate, the antenna coupled to the one or more electronic components. In some embodiments, each of the first electrode and the second electrode comprises a conductive film deposited on the substrate. In some embodiments, each of the first electrode and the second electrode comprises a metallic foil bonded to the substrate. In some embodiments, the flexible substrate is attached to the filament to define a circumferential path, and the first electrode and the second electrode are misaligned with respect to the circumferential path.

According to another embodiment of the present disclosure, a wearable therapeutic device is configured to be worn on an eye, and the device includes: a ring-shaped body; a substrate mounted on, and conforming to, an exterior surface of the ring-shaped body; a first electrode positioned on an inward-facing surface of the substrate; a second electrode positioned on an outward-facing surface of the substrate, the second electrode spaced from the first electrode; an antenna positioned around the ring-shaped body; and electronic circuitry electrically coupled to the first electrode, the second electrode, and the antenna. The electronic circuitry is configured to: receive an electrical signal from the antenna; and selectively activate at least one of the first electrode or the second electrode to stimulate the patient's tissue.

In some embodiments, the antenna is disposed in the substrate. In some embodiments, the device further includes: a first conductive trace disposed in the substrate and electrically coupling the first electrode to the electronic circuitry; and a second conductive trace disposed in the substrate and electrically coupling the second electrode to the electronic circuitry. In some aspects, the substrate insulates the antenna, the first conductive trace, and the second conductive trace from one another. In some embodiments, the device further includes a polymer tubing positioned around the substrate, where the first electrode is exposed through a first opening in the polymer tubing, and where the second electrode is exposed through a second opening in the polymer tubing. In some embodiments, the device further includes a housing, where the electronic circuitry is contained within the housing, where the housing projects inward toward a center of the ring-shaped body, and where the device comprises a circular outer profile.

In some embodiments, each of the first electrode and the second electrode comprises a conductive film deposited on the substrate. In some embodiments, each of the first electrode and the second electrode comprises a metallic foil bonded to the substrate. In some embodiments, the substrate includes: a narrow portion; a first widened portion; and a second widened portion spaced from the first widened portion. In some aspects, the narrow portion extends between the first widened portion and the second widened portion. In some aspects, the first electrode is disposed on the first widened portion, and the second electrode is disposed on the second widened portion. In some embodiments, the first widened portion and the second widened portion comprise a width, and wherein the width is less than a tubular circumference of the ring-shaped body.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 8 is a flow diagram illustrating a method for manufacturing a multidirectional nerve stimulation device, according to some aspects of the present disclosure.

DETAILED DESCRIPTION

Figure 1:
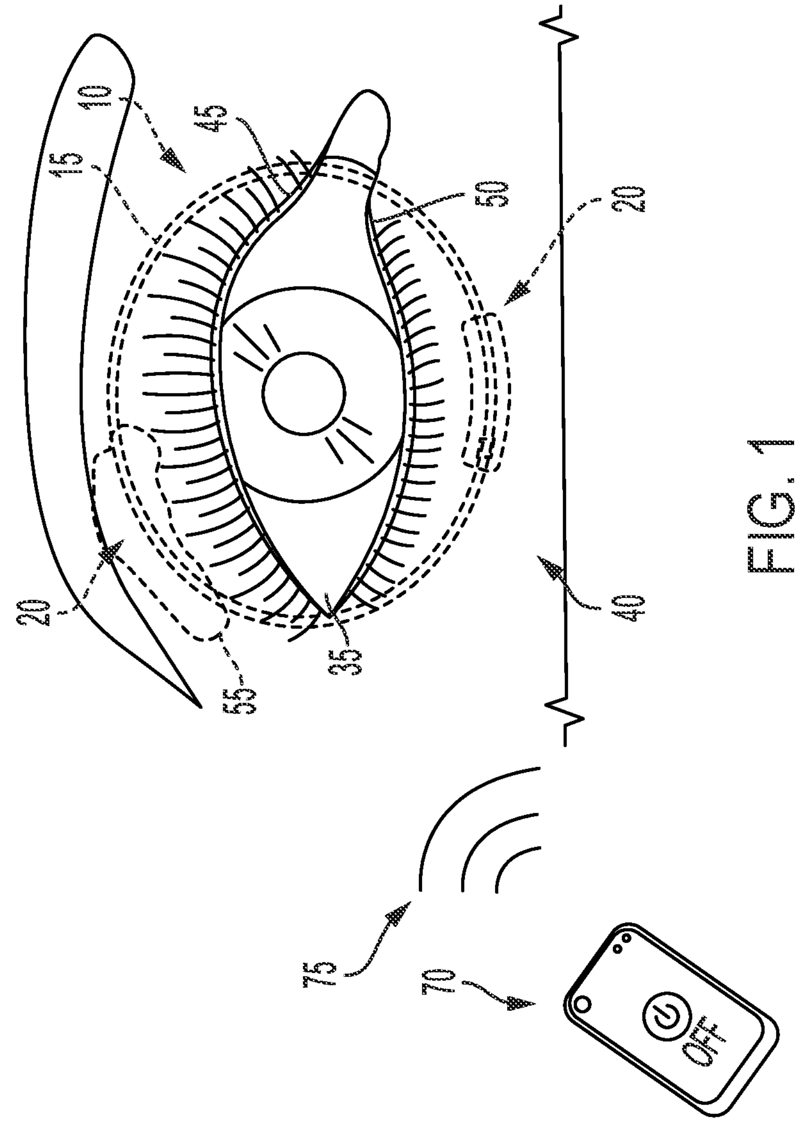
FIG. 1 is a perspective view of a therapeutic device for stimulating nerves in and around a patient's eye and a wireless remote control device providing electrical power to the therapeutic device, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Disclosed herein are devices for placement underneath the eyelid. The devices include one surface for facing the eyelid and another surface for facing the sclera. In some embodiments, the devices include electrodes configured to stimulate the sclera to induce tear production. The devices may be configured to induce electrical currents into the eye tissue or other tissue of the patient at different depths, intensities, and/or frequencies. It may be advantageous for the devices disclosed herein to have relatively small footprints to fit within the confined spaces available within the eyelid, to be flexible and thin to enhance patient comfort, and to generate sufficient voltage and/or current to stimulate the patient's nerve and achieve a desired physiological response.

A device generally referred to by the reference numeral 10, as illustrated in FIG. 1, is an example ring-shaped periocular device for neurostimulation. When mounted on the eye, the device 10 is not visible or noticeable to the user or others. Moreover, the device 10 does not obstruct the view of the user, as the device 10 does not extend over the pupil, iris, limbal ring, etc. As such, the device 10 can be used simultaneously with traditional vision correction devices, such as contact lenses and eye glasses. The device 10 is insertable in the periocular space and easily removable for cleaning and/or recharging. Thus, insertion and removal of the device 10 can be performed without the need for surgery. In some instances, the user can insert and remove the device 10 in their home. The device 10 also provides for hands-free stimulation. That is, as the device 10 includes electrodes for stimulating the lacrimal gland and a microcontroller that controls the stimulation, and the user is not required to perform any activity to activate the electrodes. The stimulation can be based on a predetermined schedule that is stored in the device 10 or can be in response to a detected or predicted dry eye condition. For example, while the user is performing another activity, such as viewing a graphical display of his or her mobile phone, the camera of the mobile phone may detect a blink rate that indicates the user is experiencing a dry-eye symptom. In response, the mobile phone wirelessly instructs the device 10 to activate the electrodes to stimulate the lacrimal gland. In some instances, the user is not aware of the detection, instruction, and activation. A user may utilize a device 10 in one eye or a device in each eye (i.e., a user may use two devices 10, one for each eye), as needed. For ease of description, the disclosure focuses on the application of device 10 to one eye, with the understanding that the disclosure may apply to both eyes of a user.

In an example embodiment and as illustrated in FIG. 1, the device 10 generally includes a wearable band or ring 15 and a gland stimulator assembly 20. In some embodiments, the stimulator assembly 20 is considered part of the ring 15, as the stimulator assembly 20 is attached physically and electrically to the ring. The term "ring" used herein refers generally to a substantially circular shape but it not so limited and may refer to an elliptical shape circumscribing, and spaced from, portions of the eye, such as the limbal ring. Generally, the device 10 is configured to encircle the front of an eye 35 of a user 40 in the ocular fornix area. For example, the device 10 may be worn outside the periphery of a user's iris, circumscribing the iris and spaced radially away from the iris. The device 10 is positioned such that the gland stimulator assembly 20 is in close enough proximity to a lacrimal gland 55 of the user 40 to stimulate tear production when electrical signals are applied to the stimulator assembly. As is understood in the art, electrical stimulation of a lacrimal gland 55 is known to increase tear production.

Referring still to FIG. 1, a wireless remote device 70 is shown providing electrical power to the device 10. The wireless remote device 70 provides power in the form of electromagnetic waves or energy 75. The electromagnetic energy 75 may pass through the device 10, which may include an antenna as further described below. The antenna may harvest the electromagnetic energy 75 and convert the electromagnetic energy 75 into an electrical current or voltage. The electrical current or voltage is provided to the electronic components of the gland stimulator assembly 20. In some aspects, the wireless remote control device 70 may also provide instructions to the device 10, and/or receive data from the electronic components of the gland stimulator assembly 20. The wireless remote device may be configured such that the electromagnetic energy 75 emitted remains below safety thresholds established by government agencies such as the U.S. Food and Drug Administration (FDA), for example.

In some aspects, the wireless remote control device 70 may be configured with smart stimulation features. The wireless remote control device 70 may include a smart phone, or may provide for wireless connectivity with the smart phone (e.g., Bluetooth) using a smartphone app. The remote control device 70 may include a variety of stimulation waveforms for magnetic pulsing and algorithms. A handheld wand may include various treatment tracking features, such as an accelerometer to track the remote control device's 70 treatment motion, and/or a wireless connection with a cellphone to give better treatment advice (determine where "blindspots" are in treatment). The wireless remote control device may track treatment time(s) and duration, and send reminders. In some embodiments, the stimulator assembly 20 may include an electrical power storage, such as a battery or a capacitor, configured to provide power to one or more components of the device 10 when the remote control device 70 is not providing power to the device 10.

The disclosed devices, systems, and methods are for treating conditions of a patient's DED using a chronotherapeutic approach. The chronotherapeutic approach is implemented by the device 10, which delivers gland stimulation at the time when it is needed. That is, gland stimulation is synchronized with circadian rhythms, among other factors, in some embodiments. If the peak of symptoms occurs at daytime for example, gland stimulation can be performed just before or when the symptoms are worsening, depending on the delay between stimulation of the gland and production of additional tear fluid.

Figure 3:
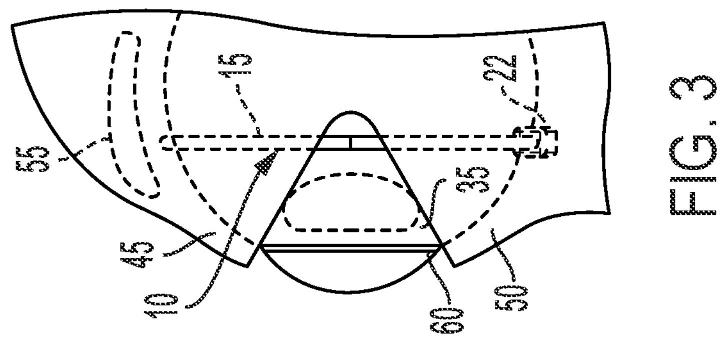
FIG. 3 is a lateral elevation view of a therapeutic device being worn inside a patient's eyelid, according to aspects of the present disclosure.
Figure 2:
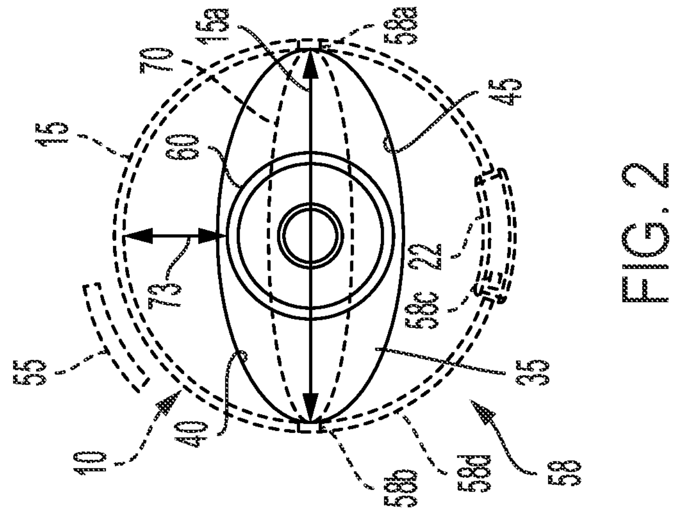
FIG. 2 is an elevation view of a therapeutic device for stimulating nerves in and around a patient's eye, according to some aspects of the present disclosure.

Referring generally to FIGS. 1-3, in some embodiments, the ring 15 forms an opening and has an inner diameter **15*a* (shown in FIG. 2) that is generally within the range of between about 24 mm to about 30 mm. However, the inner diameter 15*a* may be greater than 30 mm or less than about 24 mm. Generally, the ring 15 contacts an ocular surface of the eye, with a portion of the eye 35 extending through the opening of the ring 15. As illustrated, an innermost surface of the ring 15 is spaced from a limbal ring 60 of the eye 35 by a distance 73 (shown in FIG. 2) such that the ring 15 or device 10 does not extend over the iris and/or the limbal ring 60 of the eye 35. As such, both the iris and the limbal ring 60 are unobstructed by the device 10. Generally, the distance 73 varies with movement of the eye 35. That is, the ring 15 remains generally stationary even as the eye 35 and the ocular surface move. In some embodiments, placement and/or movement of the ring 15 is independent from the movement of the eye 35. In some embodiments, the ring 15** has a generally consistent cross-sectional shape and size.

However, in other embodiments, a portion of the ring 15 has a cross-sectional shape that is different than a cross-sectional shape of another portion of the ring 15. Moreover, the inner diameter 15*a* of the ring 15 may vary independently from an outer diameter of the ring 15.

A nerve stimulation device, such as the device 10, could be used to treat various conditions related to nerve and/or tissue dysfunction in and around the eye 35, such as dry eye. The conditions may be treated by stimulating, for example, the lacrimal gland, infrachochlear nerve, long ciliary nerve bundles, ethmoidal nerve, and other nerves or tissues in and around the eye. The various nerves and tissues that can be potentially treated are located at different locations in and around the eye. Further, suitable treatment or stimulation may involve stimulating the nerves by inducing currents have different pathways or directions. The present disclosure describes multidirectional nerve stimulation devices that include a plurality of electrodes located at different positions around an annular wearable device, such as the device 10. Further, the electrodes may be oriented in different directions relative to the center or central axis of the device 10 (e.g., radially inward, outward, upward, etc.). Embodiments of the present disclosure allow for a multi electrode, multidirectional nerve stimulation device in which the placement and orientation of the electrodes can be arbitrarily set with simplified and reliable manufacturing techniques.

Figure 4:
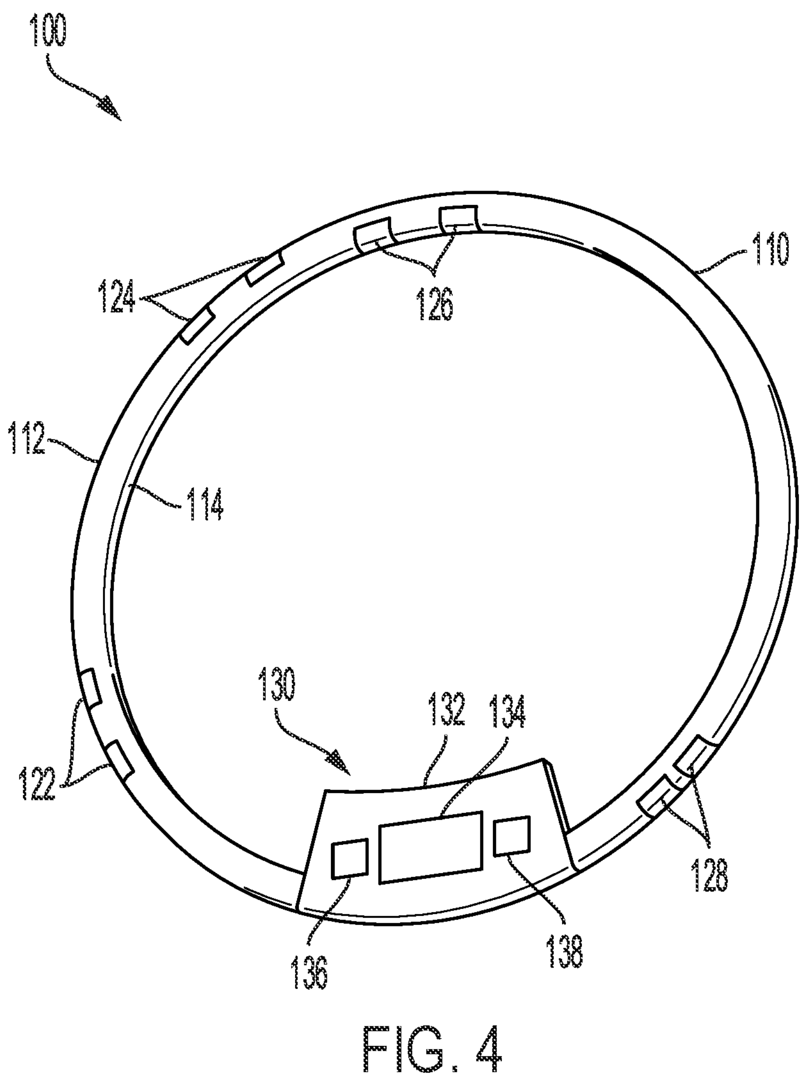
FIG. 4 is a perspective view of a multidirectional nerve stimulation device configured to be worn inside a patient's eyelid, according to some aspects of the present disclosure.

FIG. 4 is a top elevation view of a multidirectional periocular stimulator device 100, according to one aspect of the present disclosure. The device 100 is configured to emit stimulating electrical currents from one or more radial positions around the periocular device 100, and in one or more directions relative to the annular body 110 of the periocular device 100. The device 100 includes the annular body 110, which may include a flexible filament, wire, or other elongate member, a plurality of electrode pairs 122, 124, 126, 128, and an electronic subassembly 130, including electronic components 134, 136, 138, positioned with in a housing 132. The device 100 is configured to emit stimulating current radially outward (e.g. outward from an outer surface 112), radially inward (e.g., towards the center of the annular body 110 from an inner surface 114 of the annular body 110), or at any suitable orientation or pathway, which is at least in part based on the position of the electrodes relative to the outer/inner surfaces 112, 114 of the body 110.

The electrode pairs 122, 124, 126, 128 may be activated individually, altogether, or in subgroups. For example, in some aspects, the electrode pair 122 is configured to be activated at a same time as electrode pair 126. Each electrode of the electrode pairs 122, 124, 126, 128, may be configured to be activated individually, or both electrodes of each pair may be configured to be activated simultaneously. In the example illustrated in FIG. 4, the electrode pair 128 is a counter electrode pair, such that stimulating current is configured to travel from electrode pairs 122, 124, and/or 126 to counter electrode pair 128. In some aspects, the counter electrode pair 128 is configured with a polarity that is opposite that of the electrode pairs 122, 124, and/or 126. In other aspects, the counter electrode pair 128 may be configured as neutral or ground. Further, in some embodiments, one or more of the electrodes of the pairs 122, 124, 126, 128 may be a sensor electrode configured to detect tear film, blink rate, and/or pH, for example.

Each electrode pair 122, 124, 126, 128 is positioned at a different angular orientation about a circumference of the body 110. The various electrode pairs 122, 124, 126, 128 may be positioned to stimulate specific nerves, nerve groups, and/or tissue when the device 100 is positioned on the eye, under the eyelid, and/or within the periocular space in a desired angular orientation. For example, the electrode pair 122 may be positioned to stimulate the infra-trochlear nerve and/or the nerves ending in the conjunctiva. Additionally, the electrode pair 124 may be configured to stimulate the lacrimal glands, and the electrode pair 126 may be configured to stimulate the long ciliary nerve bundles in the periocular space. Additionally, electrode pair 126 may be positioned to stimulate the infra-trochlear nerve and/or the nerves ending in the conjunctiva. However, it will be understood that these are merely exemplary, and that other configurations are also contemplated by the present disclosure.

The electrode pair 122 and electrode pair 124 are positioned on an outer surface 112 of the body 110, such that the electrode surfaces of the pairs 122, 124 emit electrical currents radially outward from the outer surface 112. By contrast, the third electrode pair 126 is positioned over an inner surface 114 of the body 110, such that the electrode surfaces of the pair 126 emit electrical currents radially inward from the inner surface 114. The counter electrode pair 128 is also shown as outward-facing. However, it will be understood that the configuration shown in FIG. 4 is exemplary, and the positions, orientations, spacing, and/or other geometrical aspects of the electrode pairs 122, 124, 126, 128 may be modified within the scope of the present disclosure. The electrodes may include a conductive film or foil deposited on or mounted to a substrate, as further explained below. Further, the electrodes may include coated or insulated portions and non-insulated or exposed portions in contact with the surrounding tissue and fluids. In some aspects, the exposed portions may occupy an entirety of the surface area of at least one side each electrode. In other aspects, the exposed portions occupy a non-complete portion of the surface area of each electrode.

The electrode pairs 122, 124, 126, and/or 128 are controlled, activated, or otherwise manipulated by the electronic circuitry 130. Electronic circuitry 130 includes a plurality of electronic components 134, 136, 138, positioned within a housing 132. The housing 132 may include a polymer shell or body. The polymer shell or body may be rigid or flexible. In an exemplary aspect, the housing 132 is flexible and biocompatible to provide for enhanced comfort when worn by the user. Electronic components 134, 136, 138 may include one or more processors, such as application-specific integrated circuits (ASICs), field-programmable gate arrays (FPGAs), or a general-purpose processor; transceivers, power management circuits, memory, sensors, electrodes/electrode pairs, or any other suitable electronic component. As further explained below, electronic circuitry may be electrically coupled to an antenna, such as an antenna loop extending around the circumference of the body 110. The antenna may supply electrical power to the electronic circuitry 130, which may then provide electrical current or voltage to the electrode pairs 122, 124, 126, 128.

The electronic circuitry 130 may be configured to provide electrical current or voltage selectively to individual electrodes, or electrode pairs 122, 124, 126, 128 based on instructions stored in a memory. The instructions may include operating parameters, such as the electrodes or electrode pairs to be activated, electrical pulse waveform, pulse duration, intensity, frequency, and/or any other suitable parameter. The instructions may specify a protocol or program determined by the user and/or the physician. The instructions may be associated with a treatment regimen to treat one or more ophthalmic ailments, such as dry eye. The device 100 may be programmed, or the instructions may be modified via the wireless remote control device 70 shown in FIG. 1, for example. In some aspects, one or more of the electronic components 134, 136, 138, includes a transceiver (e.g., Bluetooth® low energy) configured to receive, decode, and process radiofrequency signals from the wireless remote control device, the instructions including nerve stimulation operating parameters as described above. For example, the device 100 may receive radiofrequency signals from the wireless remote control device, and the electronic circuitry 130 may provide electrical signals or pulses to one or more of the electrode pairs 122, 124, 126, and/or 128 via electrical leads or traces extending from the electronic circuitry 130 to the electrode pairs 122, 124, 126, and/or 128.

Figure 5A:
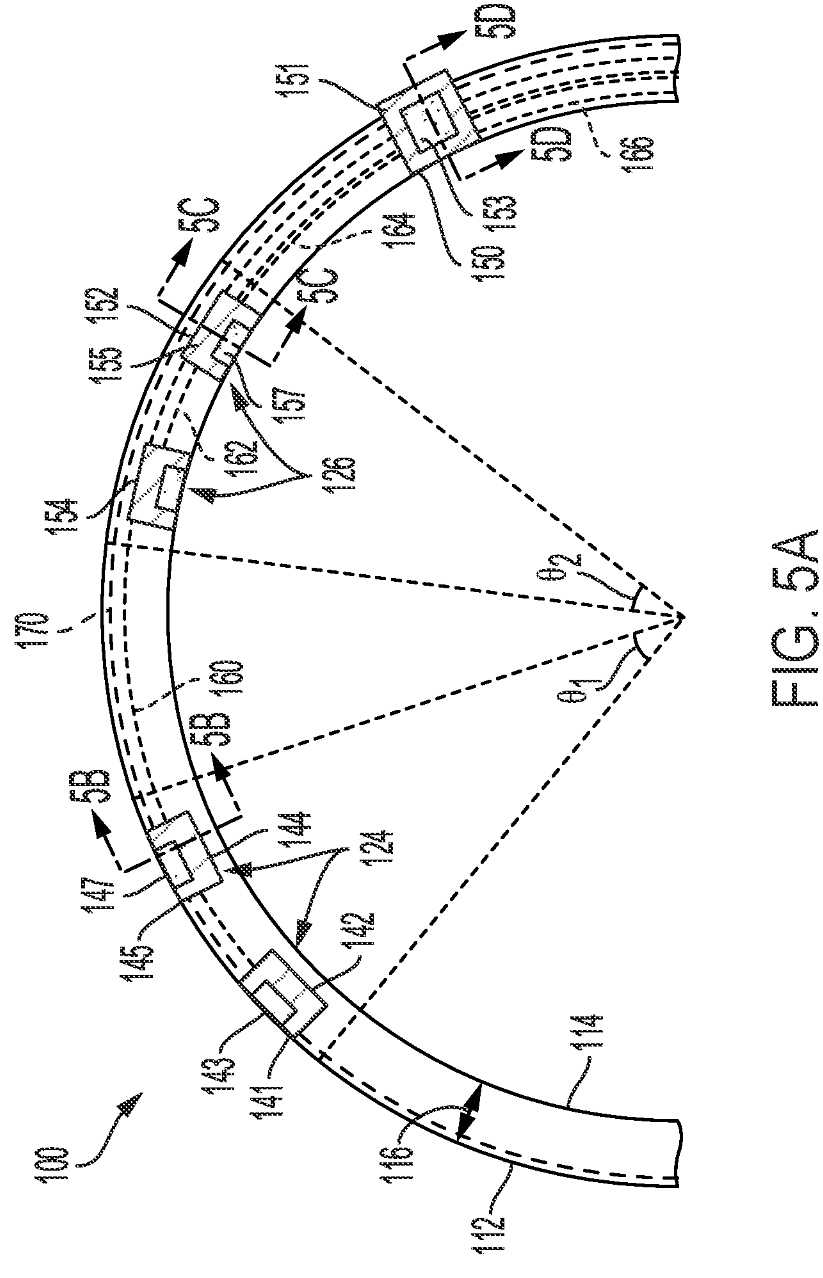
FIG. 5A is a top plan view of a portion of a multidirectional nerve stimulation device, according to some aspects of the present disclosure.

FIG. 5A is a top elevation view of the multidirectional periocular stimulator device 100, according to another embodiment of the present disclosure. The device 100 includes the annular body 110, which may include a flexible filament, wire, or other elongate member, electrode pairs 124 and 126, and an electrode 150. The device 100 is configured to emit stimulating current radially outward (e.g. outward from an outer surface 112), radially inward (e.g., towards the center or central axis of the annular body 110 from an inner surface 114 of the annular body 110), and/or upward, orthogonal to a horizontal plane of the device 100. The device 100 further includes a plurality of electrical traces 160, 162, 164, 166, and an antenna loop 170. The electrical traces 160, 162, 164, 166 are electrically coupled to the various electrodes or electrode pairs (e.g., 142, 150) and electronic circuitry (e.g., 130, FIG. 4). The loop antenna 170 is also electrically coupled to the electronic circuitry.

The electrode pairs 124, 126 include individual electrodes (e.g., 142, 144), each including an insulated or covered surface portion (e.g., 141, 145), and an exposed surface portion (e.g., 143, 147.). In this regard, the electrodes 142, 144 may include a metallic film or foil in communication with a respective electrical trace (e.g., 160). The electrodes 142, 144 may include an insulating layer, such as a polymer tubing or coating, disposed over at least a portion of the electrodes 142, 144. In some embodiments, the exposed electrode surface portions 143, 147 are formed by removing (e.g., ablating, cutting, etching) the insulating layer over at least a portion of the electrode surface, such that the conductive electrode surface is exposed to the surrounding tissue and/or fluids through the etched opening. Similarly, the electrode 152 of the electrode pair 126 includes an insulated surface portion 155 and an exposed surface portion 157, and the electrode 150 includes an insulated surface portion 151 and an exposed surface portion 153.

The electrodes 142, 144 of the electrode pair 124 are outward-facing, such that the electrodes 142, 144 are configured to emit electrical currents from an outer surface 112 of the body 110. As FIG. 5A is a top elevation view, it will be understood that each of the electrodes 142, 144 extend at least partially around the outer surface 112 of the body 110. For example, in some aspects, the electrodes 142, 144 may be centered on an outer perimeter of the body 110, and only the top portions of the electrodes 142, 144 are shown in FIG. 5A. In other embodiments, the electrodes 142, 144 may not be centered on the outer perimeter, but may otherwise be configured to emit electrical current in a direction generally outward from the outer surface 112 of the body 110. The electrodes 152, 154 of the pair 126 are inward-facing, such that the electrodes 152, 154 are configured to emit electrical currents from the inner surface 114 of the body 110. As similarly explained above, it will be understood that each of the electrodes 152, 154 extend at least partially around the inner surface 114 of the body 110. For example, in some aspects, the electrodes 152, 154 may be centered on an inner perimeter of the body 110, and only the top portions of the electrodes 152, 154 are shown in FIG. 5A. The electrode 150 is upward-facing, such that electrode 150 is configured to emit electrical currents from a top surface or portion of the body 110, where the top surface or portion is the portion visible in FIG. 5A. The toroidal angular orientation of the electrodes 142, 144, 152, 154 will be described further with respect to FIGS. 5B-5E.

Referring still to FIG. 5A, both of the electrodes 142, 144 are coupled to the electronic circuitry via a first conductive trace 160. The inclusion of two electrodes 142, 144, although activated by a common conductive trace 160, may allow for stimulation from a greater surface area for improved treatment, while maintaining the flexibility of the device. In this regard, a single electrode occupying the same angular orientation $\theta_1$ may be more rigid, and more difficult to deform into a rounded shape suitable to be worn comfortably. Accordingly, the electrodes 142, 144 are activated as a pair, by providing electrical power from the circuitry to the electrode pair 124. The electrodes 152, 154 of the electrode pair 126 are coupled to electronic circuitry via a second conductive trace 162 and a third conductive trace 164, where the second conductive trace 162 is independent of the first conductive trace 160 and the third conductive trace 164. Accordingly, the electrodes 152, 154 of the pair 126 may be configured to be activated independently. The electrode 150 is electrically coupled to the electronic circuitry by a fourth conductive trace 166.

The device 100 further includes an antenna loop or trace 170, which extends around a circumference of the device 100. Although shown as a single line, it will be understood that the antenna loop 170 may include multiple concentric loops. For example, the antenna loop 170 may form a spiral that circles the circumference two times, three times, four times, five times, or any other suitable number of loops. In other embodiments, the antenna comprises multiple concentric loops or curves that are not arranged in a spiral. The traces 160, 162, 164, 166, and the antenna loop 170 may include one or more metallic layers deposited or mounted on a substrate, for example. The traces 160, 162, 164, 166, and/or the antenna loop 170 may include a metallic film or foil that is deposited on the substrate by a mechanical, chemical, or other process (e.g., sputtering, chemical vapor deposition, bonding). In an exemplary embodiment, the traces 160, 162, 164, 166, and/or the antenna loop 170 include one or more gold layers of material. However, any suitable conductive material may be used, including platinum or copper, or any other suitable conductive material or alloys thereof. The traces 160, 162, 164, 166, and the antenna loop 170 may be deposited or mounted on the substrate in a single manufacturing step, or in different manufacturing steps. In some embodiments, the antenna loop 170 is deposited or bonded to a first side of the substrate (e.g., an underside positioned against a filament), and the traces 160, 162, 164, 166 are deposited or bonded to an opposite second side of the substrate. Further details regarding the electrical connections between the traces 160, 162, 164, 166, and the antenna loop 170 will be provided below with respect to FIGS. 7, 10, and 11.

The electrode pairs 124, 126, are positioned at different angular portions of the device 100. In this regard, the electrode pair 124 is positioned at a first angular portion $\theta_1$, and the electrode pair 126 is positioned at a second angular portion $\theta_2$. The angular portions $\theta_1$ and $\theta_2$ may be associated with or defined by both a central angle with respect to the center of the annular-shape of the device 100, and the angular width or portion of the circumference occupied by the respective electrodes. The angular portions $\theta_1$ and $\theta_2$ may correspond to different nerves or nerve bundles, or different tissues to be treated. In that regard, the electrode pair 124 positioned at $\theta_1$ may be configured to treat a first condition by stimulating a first nerve, nerve group, or tissue (e.g., lacrimal gland), the electrode pair 126 positioned at $\theta_2$ may be configured to treat a different second condition by stimulating a second nerve, nerve group, or tissue. In some embodiments, the electrode pairs 124, 126 occupy a same angular amount (e.g., 20 degrees) of the circumference of the device 100. In other embodiments, the electrode pairs 124, 126 occupy different angular amounts of the circumference of the device 100.

Figure 5B:
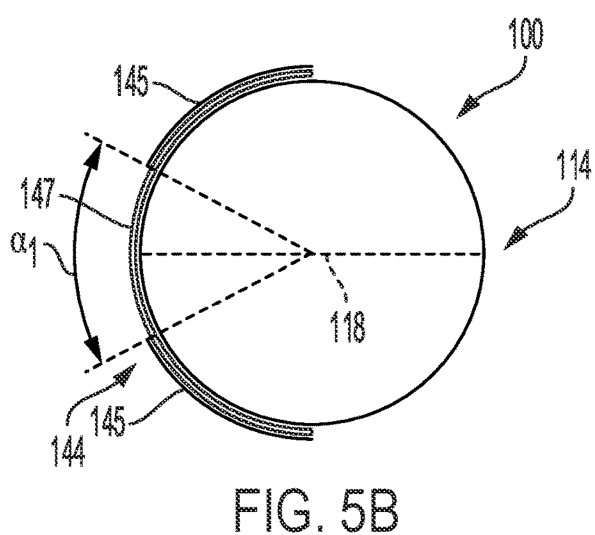
FIG. 5B is a cross-sectional view of the multidirectional nerve stimulation device of FIG. 5A taken along line 5B-5B, according to some aspects of the present disclosure.

FIGS. 5B-5E are simplified cross-sectional views of the device 100, showing the cross-sectional angular orientation (a) of the electrode surfaces with respect to a horizontal plane 118 of the device 100. FIG. 5B is a cross-sectional view of the electrode 144 of the device 100 taken along the line 5B-5B. The exposed portion 147 of the electrode 144 is oriented outward away from outer surface 112 of the device 100. In the illustrated embodiment, the exposed portion 147 occupies an angular portion $\alpha_1$, which is substantially centered along the horizontal plane 118. It will be understood that $\alpha_1$ represents both the angular portion of the circular cross-section, as well as the angle at which the exposed portion 147 is centered with respect to the horizontal plane 118. Insulated portions 145 are present above and below the exposed portion 147. In some aspects, the circular cross-section shown in FIGS. 5B-5E may be referred to as the tubular circumference of the device 100. The electrode 144 may be configured to emit an electrical current radially outward from the outer surface 112.

Figure 5C:
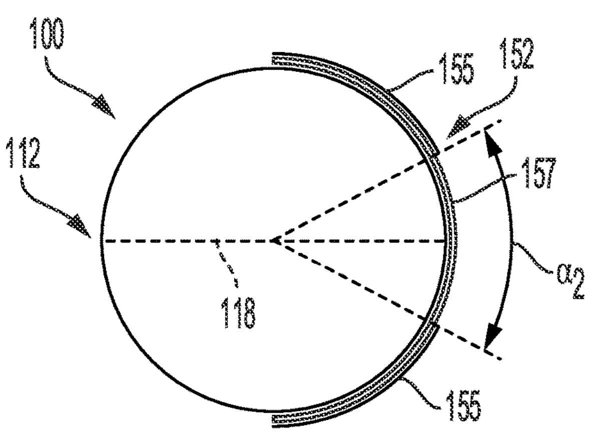
FIG. 5C is a cross-sectional view of the multidirectional nerve stimulation device of FIG. 5A taken along line 5C-5C, according to some aspects of the present disclosure.

FIG. 5C is a cross-sectional view of the electrode 152 of the device 100 taken along the line 5C-5C. The exposed portion 157 of the electrode 152 is oriented inward toward a center of the device 100, such that the electrode two is positioned over the inner surface 114 of the device 100. In the illustrated embodiment, the exposed portion 157 occupies an angular portion $\alpha_2$, which is substantially centered along the horizontal plane 118, but oriented in an opposite direction than the electrode 144 with respect to the center of the annular-shaped device 100. Insulated portions 155 are present above and below the exposed portion 157. The electrode 152 may be configured to emit an electrical current radially inward from the inner surface 114.

Figure 5D:
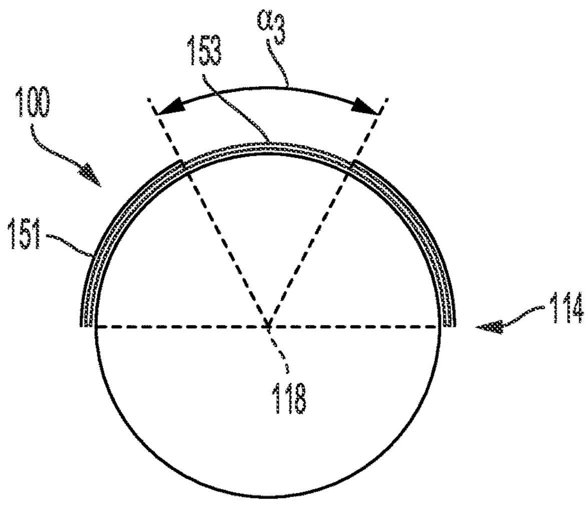
FIG. 5D is a cross-sectional view of the multidirectional nerve stimulation device of FIG. 5A taken along line 5D-5D, according to some aspects of the present disclosure.

FIG. 5D is a cross-sectional view of the electrode 150 of the device 100 taken along the line 5D-5D. The exposed portion 153 of the electrode 150 is oriented upward, approximately 90° offset from the electrodes 144 and 152. In the illustrated embodiment, the exposed portion 153 of the electrode 150 occupies an angular portion $\alpha_3$, which is centered on an angle approximately orthogonal to the horizontal plane 118. Insulated portions 151 are present on either side of the exposed portion 153. The electrode 150 may be configured to emit an electrical current upward in a direction orthogonal, or substantially orthogonal, to the horizontal plane 118.

Figure 5E:
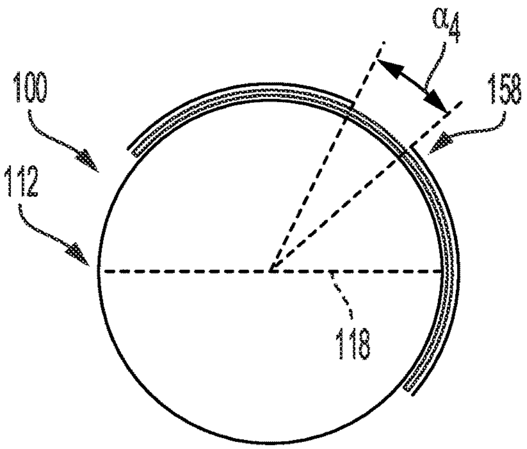
FIG. 5E is a cross-sectional view of a multidirectional nerve stimulation device, according to some aspects of the present disclosure.

FIG. 5E is a cross-sectional view of an electrode 158, which may be present on the device 100, in some embodiments. In the embodiment of FIG. 5E, the electrode 158 occupies an angular portion $\alpha_4$, which is centered at an angle oblique to the horizontal plane 118, and generally upward and radially outward. As shown, the angular portion $\alpha_4$ occupies a smaller range of angles than the angular portions $\alpha_1$-$\alpha_3$. Accordingly, the electrode 158 may be configured to emit electrical currents from a smaller or more focused surface area corresponding to the angular portion $\alpha_4$. Further, it will be understood that the embodiments shown in FIGS. 5E-5E are exemplary, and that one or more aspects of the cross-sectional angular orientation of the electrodes may be modified without departing from the scope of the present disclosure. For example, in some embodiments one or more of the electrodes 144, 150, 152 may be oriented downward, or at least partially downward. Further, the electrodes 144, 150, 152 may occupy greater or smaller angular portions than those shown in FIGS. 5B-5E. Further, in some embodiments, there may be multiple exposed portions on one or more of the electrodes, such that exposed portion occupies a different cross-sectional angular portion with respect to the horizontal plane 118.

Figure 6:
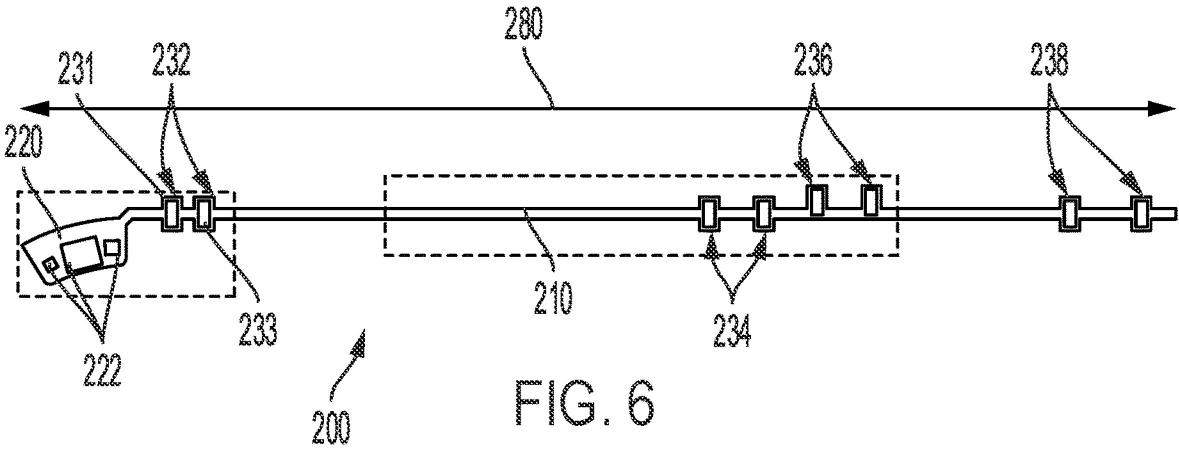
FIG. 6 is a top plan view of an electronic subassembly of a multidirectional nerve stimulation device, according to some aspects of the present disclosure.

FIG. 6 is a top plan view of an electrode subassembly 200 in a flat or pre-formed state, according to aspects of the present disclosure. In this regard, the electrode subassembly 200 is configured to be mounted, bonded, adhered, or otherwise positioned over an elongate body, such as a polymer filament, which is then formed into an annular shape. The electrode subassembly 200 may be referred to as a flex circuit, and includes an elongate substrate 210 having a widened electronic circuitry portion 220, and a plurality of widened electrode portions 232, 234, 236, 238. The substrate 210, which may also be referred to as a backing material, may include a flexible polymer material, such as a liquid crystal polymer (LCP), Parylene-C or polyimide (e.g., KAPTON®) film. The flexible substrate 210 may be biocompatible and suitable for thermoforming, or other types of material deformation and shaping.

The electrode subassembly 200 is configured to be formed into an annular shape, such as a toroidal shape. The geometry of the subassembly 200, including the widened portions 220, 232, 234, 236, 238, advantageously allow for greater flexibility and deformation to assume an annular shape with relatively high curvature. In this regard, when assembled, the relatively narrow elongate portion of the substrate 210 may be substantially less than a cross-sectional circumference of the annular shape of the assembled device. Thus, the substrate 210 can better conform to the exterior surface of the filament (see, e.g., FIG. 9B), and kinking of the polymer substrate 210 or electronic components may be reduced or eliminated, providing a smoother, more uniform exterior surface and profile to improve comfort and minimized agitation to the patient when worn. In this manner, the electronic components of the device, including the electrodes 231, 233, electronic circuitry 222, and conductive traces and vias (see 260, 228, FIG. 7), can be mounted, embedded, printed, deposited, or otherwise attached to the substrate 210 using conventional electronic circuitry manufacturing techniques, which may reduce costs and increase consistency and reliability. As similarly explained above with respect to FIG. 4, the electronic circuitry 222 may include one or more processors, such as application-specific integrated circuits (ASICs), field-programmable gate arrays (FPGAs), or a general-purpose processor; transceivers, power management circuits, memory, sensors, electrodes/electrode pairs, or any other suitable electronic component.

As shown in FIG. 6, the widened portions 232, 234, 236, 238 extend outward from the elongate portion of the substrate 210 in different directions. In this regard, the widened portions 232, 234, and 238 extend outward in both directions by a first amount from the elongate portion of the substrate 210. The widened portions 236 extend outward in only one direction by a larger second amount from the elongate portion of the substrate 210. The positioning or geometry of the widened portions 232, 234, 236, 238, correspond to the directionality of the electrode surfaces when the device is assembled, such as outward-facing (e.g., electrode pair 124, FIG. 5A), inward-facing (e.g., electrode pair 126, FIG. 5A), or upward/downward facing (e.g., electrode 150, FIG. 5A). For example, the widened portions 232, 234, and 238 are positioned such that their corresponding electrodes (e.g., 231, 233) are outward-facing, such as the electrodes of the pair 124 in FIG. 5A, and the widened portions 236 are positioned such that their corresponding electrodes are inward-facing, such as the electrodes of the pair 126 in FIG. 5A. Accordingly, the widened portions 236 and their corresponding electrodes are misaligned with the widened portions 232, 234, 238, and their corresponding electrodes (e.g., 231, 233). Thus, the subassembly arrangement shown in FIG. 6 also allows for arbitrary positioning and arrangement of electrodes, both in the angular position (0, FIG. 5A), and cross-sectional angular position (a, FIGS. 5B-5E). Further, the electronic circuitry portion 220 may also include a widened portion on which one or more electrodes, electrode pairs, and/or sensors may be positioned. Similarly, the position of the electrode surface on the electronic circuitry portion 220 may provide the angular position and orientation of the electrode/sensor on the full assembly. The arbitrary positioning and arrangement of electrodes can be achieved by a simplified manufacturing process, which may involve less human input and error than other more manual manufacturing processes.

Figure 7:
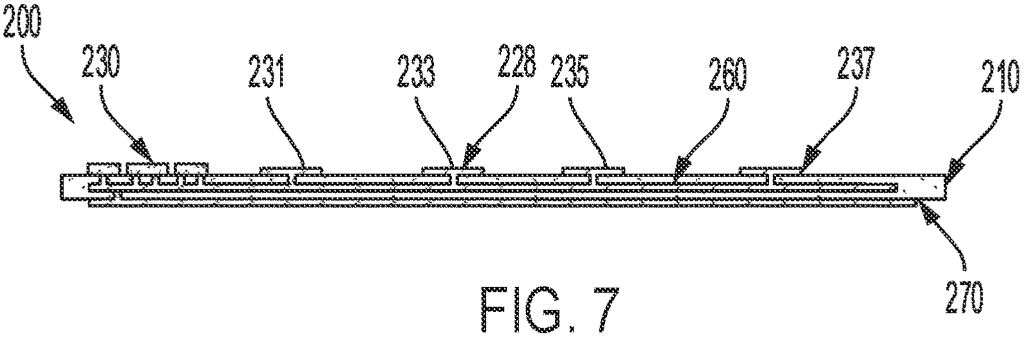
FIG. 7 is a cross-sectional view of an electronic subassembly of a multidirectional nerve stimulation device, according to some aspects of the present disclosure.

FIG. 7 is a diagrammatic, cross-sectional view of the electrode subassembly 200 shown in FIG. 6. The subassembly 200 includes a substrate or backing material 210, electronic circuitry 230, a plurality of electrodes 231, 233, 235, 237, conductive traces 260, and an antenna 270. In the embodiment of FIG. 7, the conductive traces 260 are embedded in the substrate 210, and electrically connected to the individual electrodes 231, 233, 235, 237 by vias 228. Further, the electronic circuitry 230 is electrically connected to the electrodes via the conductive traces 260 and the vias 228. The antenna 270 is disposed on an underside of the substrate 210, and the electrodes are disposed on an opposite top side of the substrate 210. The electrodes 231, 233, 235, 237 may comprise thin films or foils deposited on, mounted to, or otherwise coupled to the substrate 210. In the illustrated embodiment, all electrodes 231, 233, 235, 237 are electrically connected to a single conductive trace 260. However, it will be understood that in other embodiments, such as the embodiment shown in FIG. 5A, one or more of the electrodes 231, 233, 235, 237 may be connected to a different conductive via than the other electrodes.

FIGS. 8 and 9A-9H illustrate a manufacturing process for a multidirectional nerve stimulation device. FIG. 8 is a flow diagram illustrating a method 300 for manufacturing a multidirectional nerve stimulation device, such as the device 100, and may include or otherwise involve the subassembly 200. The steps of the method 300 are illustrated in FIGS. 9A-9H, and will be referenced throughout the description of FIG. 8.

Figure 9A:
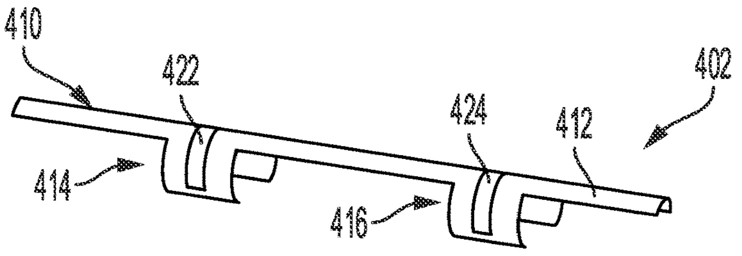
FIGS. 9A-9H illustrate various steps of the method shown in FIG. 8, according to some aspects of the present disclosure.

Referring to FIGS. 8 and 9A, at step 305, a flex circuit 402 is formed, molded, press, or otherwise deformed into a curved shape. The flex circuit 402 may be similar to the subassembly 200 shown in FIGS. 6 and 7. The flex circuit 402 includes a substrate or backing material 410 including one or more narrow portions 412, and one or more widened portions 414, 416 having electrodes 422, 424 deposited or mounted thereon. One or more conductive traces or wires are coupled to, embedded within, or otherwise positioned on the substrate 410 to connect one or more of the electrodes 422, 424 to electronic circuitry mounted on the substrate 410. The flex circuit 402 may also include an antenna trace deposited on, embedded within, or otherwise coupled to the substrate 410. The flex circuit 402 may initially be provided in a flat, planar, unrolled state, as shown in FIG. 6, for example. The substrate 410 may include a flexible polymer material which can be twisted, rolled, deformed, or otherwise manipulated to assume an annular shape, such as a toroid. Forming the flex circuit 402 into the curved shape may include positioning the flat flex circuit 402 on a mandrel, and thermoforming the flex circuit 402 to assume a curved or cylindrical shape.

Figure 9B:
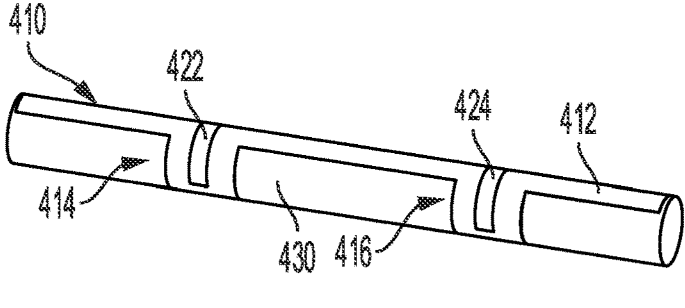

Referring to FIGS. 8 and 9B, at step 310, the deformed flex circuit 402 is mounted onto a polymer filament 430. The polymer filament 430 includes a solid body having a circular cross-section. However it will be understood that the polymer filament 430 may have other cross-sectional shapes, such as square, rectangular, triangular, hexagonal, octagonal, or any other shape. The flex circuit 402 may be mounted on the polymer filament 430 using an adhesive, thermal welding, laser welding, or any other suitable technique. The polymer filament may include materials such as Polyurethane, Polyethylene, Polyolefin co-polymers, Fluorinated ethylene propylene (FEP) or other thermoplastic polymers. In some aspects, the polymer filament may include a thickness or diameter ranging from 100-2000 microns. Further, although the polymer filament 430 may be described as "solid", in some embodiments, the power filament 430 is hollow. In some aspects, the filament 430 includes a tube or cannula.

Figure 9C:
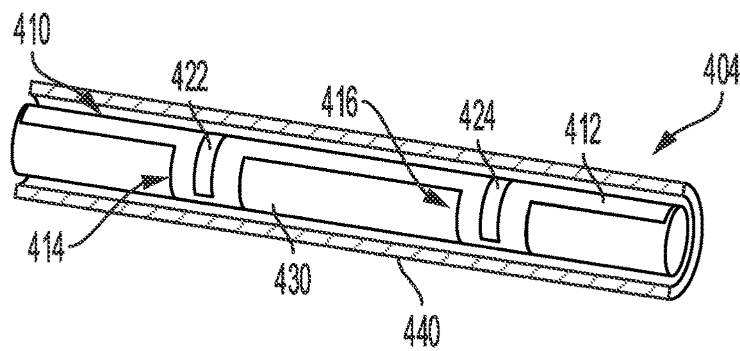

Referring to FIGS. 8 and 9C, at step 315, the subassembly, including the flex circuit 402 mounted on the polymer filament 430 is inserted into a polymer sheath 440. The polymer sheath 440 may form a protective, insulating coating for the flex circuit 402, and may also provide for a smooth outer surface to improve patient comfort. The polymer sheath 440 may have an inner diameter that provides for some clearance for the subassembly to be inserted into for ease of assembly. Further, the polymer sheath 440 may include an electronic subassembly housing portion configured to house and protect the electronic circuitry of the flex circuit 402. In other embodiments, a separate polymer housing is positioned around the circuitry.

Figure 9D:
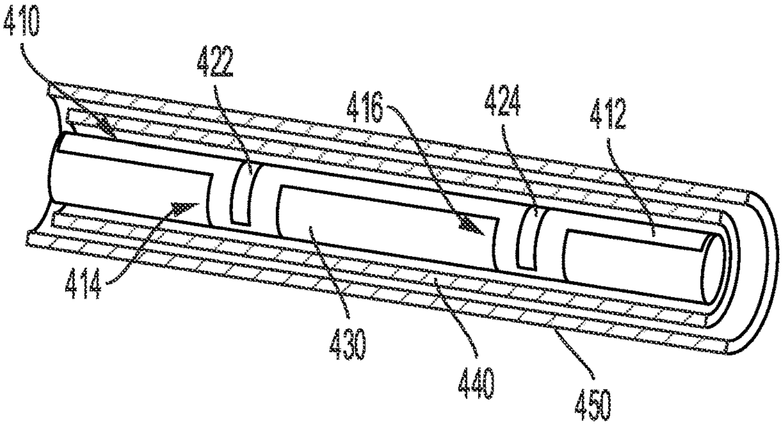

Referring to FIGS. 8 and 9D, at step 320, a heat shrink tubing 450 is positioned around the sheathed subassembly.

Figure 9E:
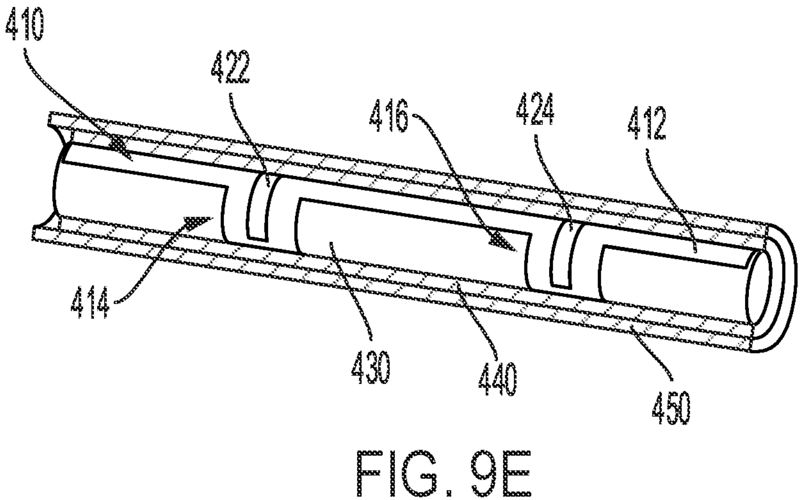

Referring to FIGS. 8 and 9E, at step 325, heat is applied to the sheathed subassembly 404 and heat shrink tube 450 to shrink the heat shrink tube 450, compress the sheath 440 around the subassembly, and bond the sheath 440 to the flex circuit 402 and/or the polymer filament 430. In some aspects, step 325 may include heating the sheath 440, the substrate 410 of the flex circuit 402, and/or the filament 430 to reflow and bond together.

Figure 9F:
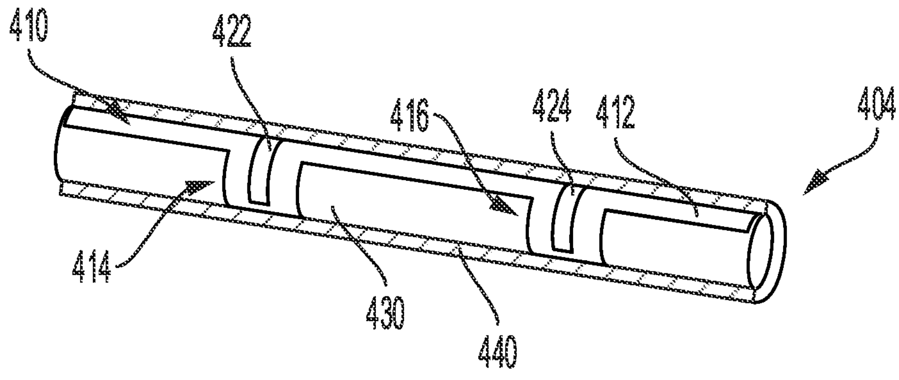

Referring to FIGS. 8 and 9F, at step 330, the shrunk heat shrink tubing 450 is removed from the sheathed assembly 404.

Figure 9G:
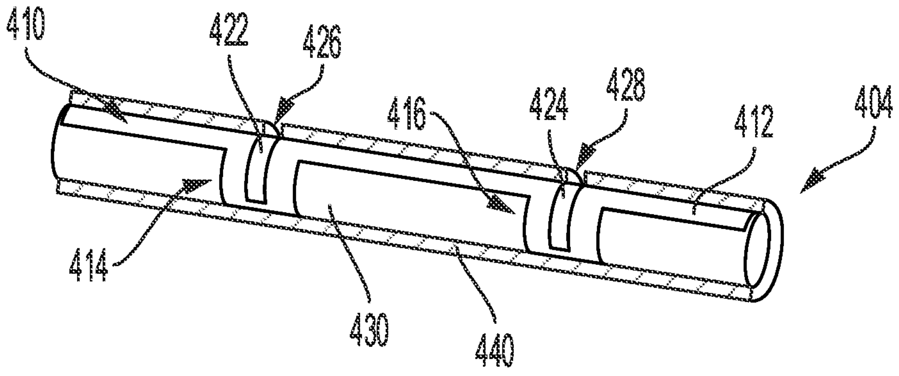

Referring to FIGS. 8 and 9G, at step 335, the polymer sheath 440 is ablated to create openings 426, 428 over the respective electrodes 422, 424. The openings 426, 428 may define exposed portions of the electrodes, as described above. In other embodiments, the polymer sheath 440 may be cut, etched, or otherwise processed to create the openings 426, 428.

Figure 9H:
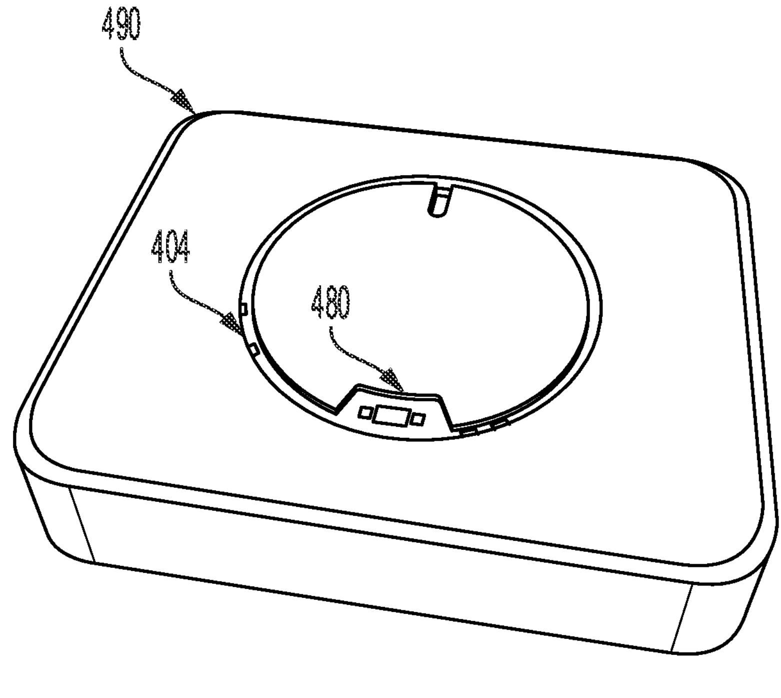

Referring to FIGS. 8 and 9H, at step 340, the sheathed subassembly 404, which includes the openings 426, 428 over the electrodes 42, 424, is placed in a mold 490 and thermoformed such that the sheathed subassembly 404 forms an annular or ring shape, which includes or defines a circumferential path. In particular, the sheathed subassembly may form a toroid, including a widened portion 480 which provides a housing for electronic circuitry. The toroid may include a circular circumference as shown in FIG. 5A, for example, and a tubular circumference as shown in FIGS. 5B-5E, for example. In some embodiments, step 340 includes soldering, welding, or otherwise electrically connecting an end of the sheathed subassembly 404 to the electronic circuitry. In particular, in some embodiments, a distal end of an antenna trace deposited on the substrate 410 is electrically connected to the electronic circuitry to form a loop antenna.

Figures 10, 11:
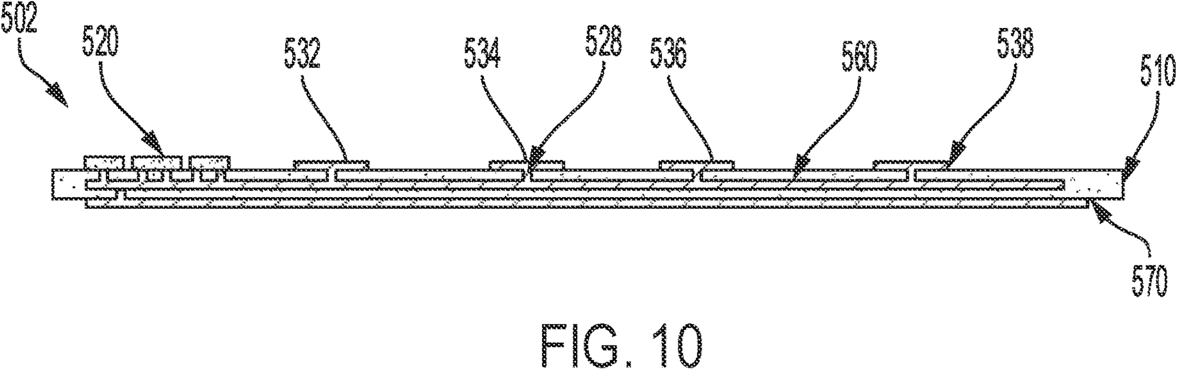
FIG. 10 is a cross-sectional view of an electronic subassembly of a multidirectional nerve stimulation device, according to some aspects of the present disclosure.
FIG. 11 is a cross-sectional view of a multidirectional nerve stimulation device, according to some aspects of the present disclosure.

FIGS. 10 and 11 at cross-sectional views of a flex circuit or subassembly 502, and multidirectional nerve stimulation device 500, respectively, according to embodiments of the present disclosure. In the embodiments of FIGS. 10 and 11, the electrodes 532, 534, 536, 538 comprise thick foils mounted on a substrate 510. Similar to the embodiments described with respect to FIGS. 5A, 6, and 7, the subassembly 502 includes electronic circuitry 520 mounted on the substrate and connected to the electrodes 532, 534, 536, 538 by electrical trace 560 and vias 528. Although only a single trace 560 is shown connecting all of the electrodes 532, 534, 536, 538, it will be understood that multiple independent traces could be used to connect individual electrodes, pairs of electrodes, or subgroups of electrodes. The subassembly 502 further includes an antenna trace 570 deposited on an underside of the substrate 510, and electrically connected to the electronic circuitry 520. The circuitry 520 may include ASICs, analog components (e.g., capacitors, resistors), transistors, field-programmable gate arrays (FPGAs), power management circuitry, batteries, transceivers, memory, or any other suitable electronic circuitry.

The thick foil electrodes may be coupled to the vias 528 via soldering, conductive adhesive, welding, or any other suitable method of attachment. In some aspects, the thick foil electrodes may comprise a thickness ranging from 0.5 microns to 50 microns. The thick foils may comprise platinum, iridium, gold, or any other suitable conductive material or alloys thereof. Thick foil conductors may provide for increased strength and durability, in some aspects.

FIG. 11 is a cross-sectional view of a multidirectional nerve stimulation device 500, which includes the subassembly 502. The subassembly 502, which includes the thick foils electrodes (e.g., 532, 534), is mounted on a polymer filament 530, and surrounded by an insulating tube or coating 540. The tube 540 is positioned around the sheathed subassembly such that the electrodes 532, 534, are exposed. The exposed portions may be formed or defined by removing portions of the insulating tube or coating 540, such as by ablation, cutting, etching, or any other suitable method. Further, the insulating tube or coating 540 may be positioned around the sheathed subassembly such that it forms a smooth, or substantially smooth, outer profile and surface with the electrodes 532, 534. In some embodiments, for example, the outer tube 540 includes a thickness that is equal, or substantially equal (e.g., +/−10%) to the thickness of the thick foil electrodes 532, 534.

The devices and systems described herein can be safely used at home and provide therapy options in a background, or on-demand (acute treatment) method. This system may also gather eye position and blink rate data for other data-driven diagnostics using one or more sensors, which may include one or more electrodes. Localized stimulation through an underlid device may not require invasiveness or anesthetic to be applied as in other prior art systems, and may allow for home-based application.

In one aspect, one or more of the devices 100, 200, 400, 500 described above can be used in an ophthalmic treatment regimen. For example, the treatment regimen may include inserting a multidirectional nerve stimulation device underneath the eyelids of the patient, such that the device is positioned on the eye and in communication with the ocular and periocular tissue. The device may include an annular shape having a size (e.g., diameter) and geometry such that the device is invisible, or substantially invisible when worn. For example, the device may have a diameter larger than the pupil and iris, and is positioned underneath the eyelids even when the patient's eyelids are open. The device may be placed by the patient, or by a physician. The device may be placed such that the electronic components of the assembly (e.g., ASICs, memory) are positioned under a bottom eyelid in a particular configuration. With the device placed in the desired position and orientation, one or more electrodes or electrode pairs may be positioned in contact with or adjacent to nerves, nerve bundles, or other tissue or anatomical structures for treatment (e.g., lacrimal gland).

In another step of the regimen, the device may be activated or powered by a wireless remote control device, which provides electromagnetic signals or energy to: (1) provide electrical power to the components of the device, and/or (2) provide instructions related to the treatment regimen, such as the specific electrodes/electrode pairs to be activated, and/or the electrical pulse structure, frequency, waveform, duration, intensity, width, etc. In some aspects, the device is powered and the instructions for treatment are carried out as long as the wireless remote control device is providing power and/or instructions to the system within an operable range. The patient may provide wireless power to the device themselves, or it may be administered by a physician. In an exemplary embodiment, the wireless remote control device is used by the patient themselves to activate the device at home, at a time when symptoms are noticed, according to a predetermined schedule, and/or at a time otherwise appropriate or convenient to the patient.

In some aspects, the electrodes stimulated correspond to the desired treatment regimen and/or the specific ailment or condition being treated. For example, if dry eye is being treated, a first electrode pair positioned in contact with or adjacent to the lacrimal gland is stimulated according to a predetermined stimulation program, which includes a stimulation pulse waveform, frequency, intensity, duration, and/or other program parameters. The program may be determined, facilitated, or selected by a physician. In other embodiments, the program may be selected by a patient based on the symptoms or condition of the patient. The program may be selected on the wireless control device using controls (e.g., buttons, knobs, touch screen, etc.)

The nerve stimulation devices, systems, and methods described herein may utilize one or more of the components, devices, systems, or methods described in U.S. Patent Application Publication No. 2020/0306537, filed Mar. 25, 2020, and U.S. Patent Application Publication No. 2020/0306538, filed Mar. 25, 2020, the entireties of which are hereby incorporated by reference.

Persons skilled in the art will recognize that the devices, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A device configured to be positioned on a surface of an eyeball of a patient without extending over an iris of the eyeball, the device being configured for directing stimulation from underneath an eyelid of the patient into a conjunctiva of the patient to stimulate nerves in or around the eyeball, the device comprising:

an annular body having a central axis therethrough; and a flex circuit mounted on and conforming to at least a portion of an outer surface of the annular body, the flex circuit comprising;

a substrate comprising an electronic circuitry portion and one or more electrode portions;

electronic circuitry disposed on the electronic circuitry portion of the substrate; and one or more electrodes bonded to the substrate at the one or more electrode portions, the one or more electrodes being separated from the position of the electronic circuitry on the substrate by an angular distance along the annular body and relative to the central axis, the one or more electrodes being electrically coupled to the electronic circuitry by one or more electrical leads extending the angular distance along the annular body, the one or more electrodes configured to apply stimulation from underneath the eyelid of the patient to the conjunctiva of the patient to stimulate the nerves of the patient, wherein an orientation around the annular body of each of the one or more electrodes is based on a position on the substrate of a respective electrode portion of the one or more electrode portions, wherein the annular body comprises a toroidal shape such that a first electrode is positioned on a radially inward-facing portion of the toroidal shape, and wherein a second electrode is positioned on a radially outward-facing portion of the toroidal shape.

2. The device of claim 1, wherein one or more of the electrodes are bonded to the electronic circuitry portion of the substrate.

3. The device of claim 1, wherein the flex circuit comprises:

a first electrode portion configured to be positioned on a first side of the substrate such that the first electrode portion is on an inward-facing portion of the toroidal shape when the flex circuit is mounted and conforming to the annular body; and a second electrode portion configured to be positioned on a second side of the substrate such that the second electrode portion is on an outward-facing portion of the toroidal shape when the flex circuit is mounted and conforming to the annular body.

4. The device of claim 1, wherein the toroidal shape comprises a tubular circumference, wherein a first exposed electrode surface of the first electrode extends over a first portion of the tubular circumference, and wherein a second exposed electrode surface of the second electrode extends over a different second portion of the tubular circumference.

5. The device of claim 1, further comprising an antenna extending along the annular body, wherein the antenna is configured to receive electromagnetic energy and provide an electrical current to the one or more electrodes.

6. The device of claim 5, wherein the flex circuit comprises:

a first conductive trace disposed in the substrate, wherein the first conductive trace electrically couples the electronic circuitry to at least one of the one or more electrodes; and a second conductive trace disposed in the substrate, wherein the second conductive trace electrically couples the antenna to the electronic circuitry.

7. The device of claim 1, further comprising a tubing positioned over the flex circuit, wherein the tubing comprises one or more openings, wherein each of the one or more openings are positioned over each of the one or more electrodes such that the one or more electrodes are exposed through the one or more openings.

8. The device of claim 1, wherein each of the one or more electrodes comprise a conductive film deposited on the substrate.

9. The device of claim 1, wherein each of the one or more electrodes comprises a metallic foil bonded to the substrate.

10. The device of claim 1, wherein the substrate is attached to the annular body to define a circumferential path, and wherein a first electrode and a second electrode are misaligned with respect to the circumferential path.

11. The device of claim 1, wherein the flex circuit comprises:

a first electrode mounted at a first electrode portion of the substrate, the first electrode portion corresponding to a first angular position around the annular body; and a second electrode mounted at a different second electrode portion of the substrate, the second electrode portion corresponding to a second angular position around the annular body, wherein the annular body comprises a filament comprising an annular shape.

12. A device configured to be positioned between an eyeball and an eyelid of a patient for directing stimulation from underneath an eyelid of the patient into a conjunctiva of the patient to stimulate nerves in or around the eyeball, the device comprising:

an annular body having a central axis therethrough; and a flex circuit mounted on and conforming to at least a portion of an outer surface of the annular body, the flex circuit comprising;

a substrate comprising an electronic circuitry portion and one or more electrode portions;

electronic circuitry disposed on the electronic circuitry portion of the substrate; and one or more electrodes bonded to the substrate at the one or more electrode portions, the one or more electrodes being separated from the position of the electronic circuitry on the substrate by an angular distance along the annular body and relative to the central axis, the one or more electrodes being electrically coupled to the electronic circuitry by one or more electrical leads extending the angular distance along the annular body, the one or more electrodes configured to apply stimulation from underneath the eyelid of the patient to the conjunctiva of the patient to stimulate the nerves of the patient, wherein an orientation around the annular body of each of the one or more electrodes is based on a position on the substrate of a respective electrode portion of the one or more electrode portions, wherein the annular body comprises a toroidal shape such that a first electrode is positioned on a radially inward-facing portion of the toroidal shape, and wherein a second electrode is positioned on a radially outward-facing portion of the toroidal shape.

13. The device of claim 12, wherein the substrate comprises:

an elongate portion;

a first electrode portion corresponding to a first widened portion; and a second electrode portion corresponding to a second widened portion spaced from the first widened portion, wherein the elongate portion extends between the first widened portion and the second widened portion, and wherein a first electrode is disposed on the first widened portion, and a second electrode is disposed on the second widened portion.

14. The device of claim 13, wherein the first widened portion and the second widened portion comprise a width, and wherein the width is less than a tubular circumference of the annular body.

15. The device of claim 12, wherein the flex circuit further comprises an antenna disposed within the substrate.

16. The device of claim 15, further comprising:

a conductive trace disposed in the substrate and electrically coupling an electrode to the electronic circuitry;

wherein the substrate insulates the antenna and the conductive trace from one another.

17. The device of claim 12, further comprising a housing, wherein the electronic circuitry is contained within the housing, wherein the housing projects inward toward a center of the annular body, and wherein the device comprises a circular outer profile.

18. A method for directing stimulation from underneath an eyelid of a patient into a conjunctiva of the patient to stimulate nerves in or around an eyeball of the patient, the method comprising:

positioning a device on a surface of the eyeball without extending over an iris of the eyeball, the device comprising:

an annular body having a central axis therethrough; and a flex circuit mounted on and conforming to at least a portion of an outer surface of the annular body, the flex circuit comprising;

a substrate comprising an electronic circuitry portion and one or more electrode portions;

electronic circuitry disposed on the electronic circuitry portion of the substrate; and one or more electrodes bonded to the substrate at the one or more electrode portions, the one or more electrodes being separated from the position of the electronic circuitry on the substrate by an angular distance along the annular body and relative to the central axis, the one or more electrodes being electrically coupled to the electronic circuitry by one or more electrical leads extending the angular distance along the annular body, wherein the annular body comprises a toroidal shape such that a first electrode is positioned on a radially inward-facing portion of the toroidal shape, and wherein a second electrode is positioned on a radially outward-facing portion of the toroidal shape; and actuating the one or more electrodes to apply stimulation from underneath the eyelid of the patient to the conjunctiva of the patient to stimulate the nerves of the patient.

19. The method for stimulating the nerves in or around the eyeball of the patient of claim 18, further comprising wirelessly connecting a remote-control device to the device, the remote-control device being configured to actuate the one or more electrodes.

* * * * *